(12) United States Patent
Hug et al.

(10) Patent No.: US 10,464,968 B2
(45) Date of Patent: *Nov. 5, 2019

(54) METHOD FOR PRODUCING A COMPOSITION FOR TREATING A TOOTH LESION

(71) Applicant: CREDENTIS AG, Windisch (CH)

(72) Inventors: Michael Hug, Zofingen (CH); Dominikus Amadeus Lysek, Windisch (CH)

(73) Assignee: Credentis AG, Windisch (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/025,344

(22) Filed: Jul. 2, 2018

(65) Prior Publication Data
US 2018/0340010 A1  Nov. 29, 2018

Related U.S. Application Data (63) Continuation of application No. 14/421,666, filed as application No. PCT/EP2013/066962 on Aug. 14, 2013, now Pat. No. 10,047,120.

(30) Foreign Application Priority Data

Aug. 15, 2012 (EP) .................... 12180578

(51) Int. Cl.
| | | |
|---|---|---|
| C07K 7/06 | (2006.01) | |
| A61K 38/17 | (2006.01) | |
| A61K 6/00 | (2006.01) | |
| A61C 5/68 | (2017.01) | |
| C07K 1/00 | (2006.01) | |
| A61K 38/00 | (2006.01) | |

(52) U.S. Cl.
CPC ............... *C07K 7/06* (2013.01); *A61C 5/68* (2017.02); *A61K 6/0017* (2013.01); *A61K 38/17* (2013.01); *C07K 1/00* (2013.01); *A61K 38/00* (2013.01); *C03C 2205/06* (2013.01); *Y10S 522/908* (2013.01)

(58) Field of Classification Search
CPC ............ A61K 2039/6031; A61K 38/00; A61K 6/0017; A61K 2039/55516
See application file for complete search history.

(56) References Cited

U.S. PATENT DOCUMENTS

| 6,548,630 B1 | 4/2003 | Zhang et al. | |
| 10,047,120 B2* | 8/2018 | Hug .................. | A61K 38/17 |
| 2006/0154852 A1 | 7/2006 | Boden et al. | |
| 2008/0199431 A1 | 8/2008 | Capito et al. | |

FOREIGN PATENT DOCUMENTS

| EP | 2327428 A2 | 6/2011 |
| WO | 2004007532 A2 | 1/2004 |
| WO | 2006047315 A2 | 5/2006 |
| WO | 2006073889 A2 | 7/2006 |
| WO | 2006138708 A1 | 12/2006 |
| WO | 2007000979 A1 | 1/2007 |
| WO | 2008113030 A2 | 9/2008 |
| WO | 2009026729 A1 | 3/2009 |
| WO | 2010041636 A1 | 4/2010 |
| WO | 2010103887 A1 | 9/2010 |
| WO | 2011058545 A1 | 5/2011 |
| WO | 2011104711 A1 | 9/2011 |

OTHER PUBLICATIONS

Kyle et al. Recombinant self-assembling peptides as biomaterials for tissue engineering. Biomaterials 31 (2010) 9395-9405. (Year: 2010).*
Eva Meister. Methodology, Data Interpretation and Practical Transfer of Freeze-Dry Microscopy. Ph.D. Dissertation. Mar. 12, 2009. (Year: 2009).*
Aggeli, Amalia, et al. "pH as a trigger of peptide β-sheet self-assembly and reversible switching between nematic and isotropic phases." Journal of the American Chemical Society 125.32 (2003): 9619-9628.
Aggeli, Amalia, et al. "Self-Assembling Peptide Polyelectrolyte β-Sheet Complexes Form Nematic Hydrogels." Angewandte Chemie 115.45 (2003): 5761-5764.
Bell, Carol J., et al. "Self-assembling peptides as injectable lubricants for osteoarthritis." Journal of Biomedical Materials Research Part A 78.2 (2006): 236-246.
Kirkham, J., et al. "Self-assembling peptide scaffolds promote enamel remineralization." Journal of dental research 86.5 (2007): 426-430.
Kyle, Stuart, et al. "Production of self-assembling biomaterials for tissue engineering." Trends in biotechnology 27.7 (2009): 423-433.
Kyle, Stuart, et al. "Recombinant self-assembling peptides as biomaterials for tissue engineering." Biomaterials 31.36 (2010): 9395-9405.
Written Opinion of the International Searching Authority from related application PCT/EP2013/066962, dated Feb. 20, 2014.
Riley et al. Bioproduction and characterization of a pH responsive self-assembling peptide. Biotechnol Bioeng. Jun. 1, 2009; 103(2):241-51.
Kyle et al. Recombinant self-assembling peptides as biomaterials for tissue engineering. Biomaterials. 2010 31:9395-9405.

* cited by examiner

*Primary Examiner* — Marcela M Cordero Garcia
*Assistant Examiner* — Jia-Hai Lee
(74) *Attorney, Agent, or Firm* — Thomas|Horstemeyer, LLP (57) ABSTRACT

The invention relates to a method for preparing a composition for treating a tooth lesion, said composition comprising peptides that are capable of undergoing self-assembly at a certain pH. The compositions of the invention are highly suitable for being used in the medical field, in particular for remineralising a tooth lesion such as a subsurface caries lesion.

7 Claims, 3 Drawing Sheets

Specification includes a Sequence Listing.

| | |
|---|---|
| P₁₁-4 (SEQ ID NO:1) | Gln-Gln-Arg-Phe-Glu-Trp-Glu-Phe-Glu-Gln-Gln |
| P₁₁-4, modified (SEQ ID NO:2) | CH₃CO-Gln-Gln-Arg-Phe-Glu-Trp-Glu-Phe-Glu-Gln-Gln-NH₂ |

SEQUENCE LISTING

```
<160> NUMBER OF SEQ ID NOS: 5

<210> SEQ ID NO 1
<211> LENGTH: 11
<212> TYPE: PRT
<213> ORGANISM: artificial
<220> FEATURE:
<223> OTHER INFORMATION: designed self-assembling peptide P11-4

<400> SEQUENCE: 1

Gln Gln Arg Phe Glu Trp Glu Phe Glu Gln Gln
1               5                   10

<210> SEQ ID NO 2
<211> LENGTH: 11
<212> TYPE: PRT
<213> ORGANISM: artificial
<220> FEATURE:
<223> OTHER INFORMATION: designed self-assembling peptide P11-4mod
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (11)..(11)
<223> OTHER INFORMATION: AMIDATION

<400> SEQUENCE: 2

Gln Gln Arg Phe Glu Trp Glu Phe Glu Gln Gln
1               5                   10

<210> SEQ ID NO 3
<211> LENGTH: 5
<212> TYPE: PRT
<213> ORGANISM: artificial
<220> FEATURE:
<223> OTHER INFORMATION: designed self-assembling peptide
<220> FEATURE:
<221> NAME/KEY: VARIANT
<222> LOCATION: (1)..(1)
<223> OTHER INFORMATION: amino acid with acidic side chain
<220> FEATURE:
<221> NAME/KEY: VARIANT
<222> LOCATION: (2)..(2)
<223> OTHER INFORMATION: amino acid with hydrophobic side chain that is
      selected from the group consisting of alanine, valine, isoleucine,
      leucine, methionine, phenylalanine, tyrosine and tryptophan
<220> FEATURE:
<221> NAME/KEY: VARIANT
<222> LOCATION: (3)..(3)
<223> OTHER INFORMATION: amino acid with acidic side chain
<220> FEATURE:
<221> NAME/KEY: VARIANT
<222> LOCATION: (4)..(4)
<223> OTHER INFORMATION: amino acid with hydrophobic side chain that is
      selected from the group consisting of alanine, valine, isoleucine,
      leucine, methionine, phenylalanine, tyrosine and tryptophan
<220> FEATURE:
```

```
<221> NAME/KEY: VARIANT
<222> LOCATION: (5)..(5)
<223> OTHER INFORMATION: amino acid with acidic side chain

<400> SEQUENCE: 3

Xaa Xaa Xaa Xaa Xaa
1               5

<210> SEQ ID NO 4
<211> LENGTH: 5
<212> TYPE: PRT
<213> ORGANISM: artificial
<220> FEATURE:
<223> OTHER INFORMATION: designed self-assembling peptide
<220> FEATURE:
<221> NAME/KEY: VARIANT
<222> LOCATION: (2)..(2)
<223> OTHER INFORMATION: amino acid with hydrophobic side chain that is
      selected from the group consisting of alanine, valine, isoleucine,
      leucine, methionine, phenylalanine, tyrosine and tryptophan
<220> FEATURE:
<221> NAME/KEY: VARIANT
<222> LOCATION: (4)..(4)
<223> OTHER INFORMATION: amino acid with hydrophobic side chain that is
      selected from the group consisting of alanine, valine, isoleucine,
      leucine, methionine, phenylalanine, tyrosine and tryptophan

<400> SEQUENCE: 4

Glu Xaa Glu Xaa Glu
1               5

<210> SEQ ID NO 5
<211> LENGTH: 5
<212> TYPE: PRT
<213> ORGANISM: artificial
<220> FEATURE:
<223> OTHER INFORMATION: designed self-assembling peptide
<220> FEATURE:
<221> NAME/KEY: VARIANT
<222> LOCATION: (2)..(2)
<223> OTHER INFORMATION: amino acid with hydrophobic side chain that is
      selected from the group consisting of alanine, valine, isoleucine,
      leucine, methionine, phenylalanine, tyrosine and tryptophan
<220> FEATURE:
<221> NAME/KEY: VARIANT
<222> LOCATION: (4)..(4)
<223> OTHER INFORMATION: amino acid with hydrophobic side chain that is
      selected from the group consisting of alanine, valine, isoleucine,
      leucine, methionine, phenylalanine, tyrosine and tryptophan

<400> SEQUENCE: 5

Asp Xaa Asp Xaa Asp
1               5
```

METHOD FOR PRODUCING A COMPOSITION FOR TREATING A TOOTH LESION

FIELD OF THE INVENTION

The invention relates to a method for preparing a composition for treating a tooth lesion, said composition comprising peptides that are capable of undergoing self-assembly at a certain pH. The compositions of the invention are highly suitable for being used in the medical field, in particular for remineralising a tooth lesion such as a subsurface caries lesion.

BACKGROUND

To date, tooth remineralisation is achieved mainly by the delivery of calcium and phosphate ions into tooth lesions or cavities. The calcium and phosphate ions are usually included in tooth pastes which also contain e.g. abrasives, fluorides, surfactants and other remineralisation agents. The calcium and phosphate ions may be used in various crystalline forms, e.g. as hydroxyapatite-based materials, or as amorphous calcium phosphate, such as in some Recaldent-based materials.

More recently, an alternative approach of tooth remineralisation has been described which is based on short rationally designed self-assembling peptides. WO 2004/007532 discloses peptides that are capable of forming three-dimensional scaffolds, thereby promoting nucleation of de-novo calcium phosphate. These artificial peptides assemble in one dimension to form beta-sheet, tape-like assemblies. The peptide assemblies can switch from a fluid to a nematic, stiffer gel state in response to chemical or physical triggers. The peptides were designed to form assemblies in response to certain pH, ionic strength and/or temperature conditions in the following hierarchical order: tapes, ribbons, fibrils and fibres. Aggeli et al. (2003, J. Am. Chem. Soc. 125, 9619-9628) analyses pH as a trigger of peptide beta-sheet self-assembly.

Several other self-assembling peptides have been described in the prior art. For example, WO 2010/041636 A1 describes a bioadsorbable peptide tissue occluding agent containing an artificial peptide having 8-200 amino acid residues with the hydrophilic amino acids and hydrophopbic amino acids alternately bonded, which self-assembles into a beta-structure at physiological pH. Self-assembling peptides with alternating hydrophobic and hydrophilic residues or stretches which interact with the extracellular matrix are also disclosed in WO 2008/113030 A2. WO 2010/103887 A1 discloses self-assembling peptides, which comprise basic, hydrophobic and acidic amino acids of a specific primary sequence and peptide gels thereof which have high strength.

Another application, WO 2007/000979 A1, describes self-assembling peptides with polar and non-polar amino acids. The peptides are capable of forming a beta-sheet structure in which the non-polar amino acid residues are arranged on one side of the structure in the assembled form. Amphiphilic self-assembling peptides for use as stable macroscopic membranes, which are used in biomaterial applications, such as slow-diffusion drug delivery, are described in U.S. Pat. No. 6,548,630.

EP 2 327 428 A2 refers to a pharmaceutical composition comprising self-assembling peptide nanofibers, which are complementary to each other, and at least one cell for repairing damaged tissue, such as tissue after a myocardial infarction.

The use of self-assembling peptides for the delivery of bioactive agents has also been described in the prior art, for example in US 2008/199431 A1 and in WO 2009/026729 A1. WO 2006/073889 A2 relates to a composition in which human PDGF is bound directly to peptides which assemble into a gel that slowly releases PDGF in vivo. WO 2006/047315 A2 proposes the attachment of therapeutic agents to self-assembling peptides using biotin/streptavidin linkages.

Kirkham et al. relates to self-assembling peptide scaffolds promoting enamel remineralisation (2007, Dent. Res. 86(5), 426-430).

As can be seen from the above, several self-assembling peptides have been described that can be used as templates or scaffolds in tooth remineralisation for in situ nucleation of calcium phosphate. However, a particular problem that one may encounter in tooth remineralisation is that subsurface lesions may be inaccessible for the assembled form of the peptides. Once these peptides have formed tapes, ribbons, fibrils or fibres, the size of the assemblies is such that diffusion into the subsurface lesion through small pores in the hypermineralised plate on the tooth surface is no longer possible in an amount necessary to achieve a significant effect.

Thus, to effectively treat subsurface lesions, the self-assembling peptide needs to be in a monomeric form outside the tooth lesion to enable diffusion into the subsurface lesion, and it needs to switch into a fibrillar form once inside the tooth lesion. If the peptides assemble outside the lesion, it cannot facilitate remineralisation within the lesion, as the formed three-dimensional structures are too large to diffuse through the pores.

Several drug transfer devices have been described in the prior art. For example, fluid transfer devices with sealing arrangements for direct application of drugs have been disclosed (e.g. WO 2011/058545 A1, WO 2011/104711 A1). However, none of these drug transfer devices eliminates the problem of assemblies outside a tooth lesion.

DESCRIPTION OF THE INVENTION

The present invention provides a method for the targeted delivery of a self-assembling peptide to a tooth lesion that enables said peptide to remain in a monomeric form outside the lesion, thereby facilitating the diffusion into the subsurface lesion. Within the subsurface lesion, the peptide switches into a self-assembled, fibrillar state. Compositions for the targeted delivery of self-assembling peptides to a tooth lesion are also provided.

In particular, in a first aspect, the present invention provides a method for producing a composition suitable for treating a tooth lesion, such as a caries lesion, comprising
a) providing a solution comprising a peptide that starts to undergo self-assembly at a pH below 7.5, wherein said solution has a pH which is 0.1 to 0.5 pH units above the pH at which the peptide starts to undergo self-assembly;
b) adding a compound that increases the pH of the solution to 8.0 or higher, said compound being sufficiently volatile to be removed during lyophilisation;
c) lyophilizing the solution; and
d) optionally, dissolving the lyophilisate in an aqueous solution to obtain a solution with a pH that is 0.1 to 0.5 pH units above the pH at which the peptide starts to undergo self-assembly, said solution comprising the peptide in its monomeric state.

The present invention is inter alia based on the insight that the use of a basic compound like ammonia, which is volatile and evaporates during lyophilisation, is helpful for controlling assembly of self-assembling peptides. In particular, by shifting the pH from basic towards more acidic conditions through evaporation of a basic compound during lyophilisation, it is possible to provide a lyophilisate which upon resuspension in water provides a homogeneous solution of predominantly monomeric peptides with a pH close to the pH at which the peptides start to undergo self-assembly. When applying this solution to a tooth surface, the monomeric peptides diffuse into the tooth lesion where remineralisation is to be achieved. In the tooth lesion, the pH is normally between 5.0 and 6.5 or lower as a result from the continuous production of lactic acid by lactic acid bacteria which form the microflora of the oral cavity. As the buffer in the reconstituted solution of the invention becomes diluted in the tooth lesion, the pH-induced assembly of the monomeric peptides starts within the lesion, thereby forming multimeric assemblies which can act as scaffolds for subsequent calcium phosphate deposition.

Even though a fresh peptide solution with a pH above the pH at which the peptide starts to undergo self-assembly will initially contain only a small percentage of self-assembled multimers, storage of the solution and exposure to the air can cause assembly due to the formation of hydrogen carbonate and subsequent acidification of the solution.

According to the method of the invention, effective monomerisation of the peptides is achieved by increasing the pH of the peptide-containing solution to 8.0 or higher. It is preferred that monomerization of the peptides is achieved by increasing the pH of the solution to a pH that is at least 0.5 units higher than the pH at which the peptide starts to undergo self-assembly. For example, when using the peptides referred to herein as SEQ ID NO:1 or SEQ ID NO:2, monomerization is achieved at a pH of 8.0 or higher, since self-assembly of these peptides starts at pH 7.5. At such high pH, more than 95%, preferably more than 96%, more than 97%, more than 98%, more than 99%, and most preferably 100% of the peptides in the solution are non-assembled, i.e. monomeric. After lyophilisation of the solution and subsequent reconstitution in water or another aqueous medium with neutral or near neutral pH, the peptides remain in a monomeric form. In this way, the present invention allows the targeted delivery of monomeric peptides into a tooth lesion and the subsequent self-assembly of said peptides within the tooth lesion, wherein the latter step is initiated by the pH in the tooth lesion without any intervention of the user, e.g. the dentist. The methods and compositions of the present invention are particularly advantageous, because the loss of significant amounts of peptides due to self-assembly of the peptides outside the tooth lesion is avoided. At the same time the methods and compositions of the present invention facilitate the necessary concentration inside the lesion body to enable self-assembly.

The method of the invention provides a composition that is highly suitable for treating a tooth lesion, such as a caries lesion, in a mammal, more preferably a human. Further, the method of the invention provides a composition that is highly suitable for mineralising a cavity in a tooth. Specifically, the methods and compositions of the invention can be used to fill tooth lesions and/or cavities with a network of interconnected peptides that promote the remineralisation of the lesion by deposition of calcium and phosphate ions, which are present e.g. in the saliva. As used herein, a caries "lesion" is a subsurface lesion or a subsurface microlesion in the tooth or the tooth surface that is normally caused by acid formation of the bacteria present in the dentalpellicle. As used herein, a tooth "cavity" is a hole in the surface of a tooth. Bacteria, in particular from the genera *Streptococcus*, *Lactobacillus* and *Actinomyces*, produce acid by fermentation of carbohydrates that originate from food. The acid formed upon fermentation results in a demineralization of the hard tooth tissues, i.e. the enamel, dentin and cementum. Tooth lesions and cavities may also be the result of a physical trauma. If left untreated, a caries lesion or cavity may lead to an infection of the pulp chamber, which contains blood vessels and nerves, which may ultimately result in tooth loss.

Generally, the lesion or cavity may be present on any tooth, e.g. on the incisors (Dentesincisivi), the canine teeth (Dentescanini), the premolar teeth (Dentespraemolares) and/or the molar teeth (Dentesmolares). Similarly, the lesion or cavity may affect any of the surfaces of a tooth, i.e. on labial, mesial, buccal, palatal, approximal and/or distal surfaces.

In a first step of the method of the invention, a solution is provided which comprises one or more self-assembling peptides. The self-assembling peptides for use in the method of the invention are selected such that they undergo self-assembly as soon as the pH of their environment drops below a certain pH, e.g. below pH 7.5. The pH at which the self-assembling peptides of the invention start to undergo self-assembly is below 7.5, preferably below 7.2, more preferably below 7.0. For example, the pH at which the self-assembling peptides P11-4 (SEQ ID NO:1) and terminally modified P11-4 (SEQ ID NO:2) start to undergo self-assembly is about 7.5. This means that the self-assembling peptides start to self-assemble to a significant extent when the pH drops below 7.5.

As used herein, "self-assembly" of the peptides refers to the spontaneous and reversible organization of peptides with other peptides of their own kind (or peptides having a similar structure) into multimeric assemblies by non-covalent interactions. Non-covalent interactions that are responsible for forming the multimeric assemblies include van-der-Waals, pi-stacking, hydrogen bonds, polar and ionic interactions between the amino acid backbones and/or the amino acid side chains of the peptides.

As used herein, the pH at which the self-assembling peptide starts to undergo self-assembly refers to the pH below which a significant extent of self-assembly of the peptides in solution is observed, which means that at least about 25%, about 30%, about 35%, about 40%, about 45%, about 50%, about 55%, about 60%, about 65%, about 70%, about 75%, about 80%, about 85%, about 90%, about 95%, about 99% or even about 100% of the peptides found in the solution are assembled. In a preferred embodiment, at least about 25% of the peptides found in the solution are assembled below the pH at which the peptide starts to undergo self-assembly.

Preferably, at the pH which initiates self-assembly, e.g. about pH 7.5 for P11-4 and modified P11-4, only about 20% or less, preferably only about 15% or less, more preferably 10% or less, and even more preferably 5% or less of the peptides are in a multimeric state. Thus, a solution in which the peptide is "predominantly" present in a monomeric form in the sense of the present invention is a solution in which only about 20% or less, preferably only about 15% or less, more preferably 10% or less, and even more preferably 5%, 4%, 3%, 2%, 1% or less of the peptides are in a multimeric state.

In contrast, below the pH which initiates self-assembly, e.g. pH 7.5 for P11-4 (SEQ ID NO:1) and modified P11-4 (SEQ ID NO:2), a significant extent of self-assembly of the peptides in solution is observed, which means that at least about 25%, about 30%, about 35%, about 40%, about 45%, about 50%, about 55%, about 60%, about 65%, about 70%, about 75%, about 80%, about 85%, about 90%, about 95%, about 99% or even about 100% of the peptides found in the solution are assembled, i.e. multimeric.

The self-assembling peptides for use in the method of the present invention preferably assemble into beta-pleated sheets. In the beta-pleated sheet, the sheet-like structure is created by a series of hydrogen bonds between residues in different polypeptide chains or between residues in different sections of a folded polypeptide. Typically, adjacent polypeptide chains in beta-pleated sheets are anti-parallel, which means that they run in opposite directions. However, the adjacent chains may also run parallel. If several polypeptide chains participate in the sheet formation, the sheet is a rigid wall-like structure. Multiple pleated sheets provide the requisite toughness and rigidity. The peptides that can be used in the method of the invention are designed to form stable secondary structures upon self-assembly. Preferably, the peptides for use in the method of the present invention will form long "beta-tapes" comprising a beta-pleated structure of a single molecule in thickness. The peptides will form complex structures during assembly, such as helical tapes (single-molecule thick), twisted ribbons (double tapes), fibrils (twisted stacks of ribbons) and fibers (entwined fibrils). With decreasing pH, helical tapes, twisted ribbons, fibrils and at last fibers may form.

The size of the self-assembling peptides that can be used in the methods of the invention is not specifically limited. The peptides of the invention may be of any length that allows self-assembly in a pH-dependent manner. Preferably, the peptides will have a size of about 4-200 amino acids, more preferably, 6-100 amino acids, 8-50 amino acids, 10-30 amino acids or 11-20 amino acids. Even more preferably, the selfassembling peptides will have a length of about 27 amino acids, 24 amino acids, 21 amino acids, 15 amino acids, or 11 amino acids. In a particularly preferred embodiment, the self-assembling peptides have a length of 11 amino acids.

The self-assembling peptides may be prepared by any suitable method that is commonly known in the field of peptide synthesis. For example, peptides with a length of more than 50 amino acids may be prepared by recombinant methods. In one embodiment, the self-assembling peptides are produced as fusion peptides. As used herein, a fusion peptide refers to a fusion of a first amino acid sequence comprising the self-assembling peptide of interest which is N-terminally or C-terminally linked to a second amino acid sequence. The second amino acid sequence may be an affinity tag, i.e. an amino acid sequence that is fused to the 5' or 3' end of the self-assembling peptide and which exhibits an increased affinity to another compound, thereby allowing purification of the fusion peptide. Preferably, the tag sequence is removed from the self-assembling peptide of interest after purification, for example by providing a proteolytic cleavage site between the self-assembling peptide and the affinity tag. In one embodiment, the self-assembling peptide is prepared as disclosed in Kyle et al., 2010, Biomaterials 31, 9395-9405.

Smaller self-assembling peptides are usually prepared by chemical synthesis. For example, the peptides may be chemically synthesized by solid phase or liquid phase methods. Protocols for solution-phase chemical synthesis of peptides have been described (see, for example, Andersson et al., Biopolymers 55:227-250, 2000). For solid phase synthesis the technique described by Merrifield (J. Am. Chem. Soc., 1964, 85, 2149-2154) may be used. In this approach, the growing peptide is anchored on an insoluble resin, and unreacted soluble reagents are removed by filtration or washing steps without manipulative losses. Solid phase peptide synthesis can be readily performed by use of automated devices.

The peptides for use in the methods of the invention may comprise any natural, proteinogenic amino acid. In addition, the peptides may also comprise unusual, non-proteinogenic amino acids, such as carnitine, gamma-aminobutyric acid (GABA), hydroxyproline, selenomethionine, hypusine, lanthionine, 2-aminoisobutyric acid, dehydroalanine, ornithine (Orn, O), citrulline, beta alanine (3-aminopropanoic acid), and the like. Non-proteinogenic amino acids can be incorporated into the peptide by post-translational modification or by direct incorporation during chemical synthesis of the peptide.

The self-assembling peptides for use in the method of the present invention preferably comprise amino acid side chains that include a —COOH group. Amino acid side chains with a —COOH will be deprotonated at pH values above their nominal pK values. For example, amino acids which comprise a —COOH group in their side chain such as aspartic acid (Asp, D) and glutamic acid (Glu, E) are essentially deprotonated at a pH above neutral, i.e. at pH 7, because they exhibit a low pKa (Asp: 3.71; Glu: 4.15). In the self-assembling peptides of the present invention, the amino acid side chains containing a —COOH group are specifically located in the peptide chain so as to control the electrostatic interactions between neighbouring peptides, i.e. so that adjacent, identical, self-assembling peptides are repelled through electrostatic interactions when the —COOH group is deprotonated to —COO$^-$, and to dominate the association free energy in bonds between peptides. Reducing the pH below a certain threshold, i.e. the pH at which the peptide starts to undergo self-assembly, such as about pH 7.5 for P11-4 (SEQ ID NO:1) and modified P11-4 (SEQ ID NO:2), leads to protonation of the —COOH group in the self-assembling peptides of the present invention which reduces the repelling electrostatic interactions between the peptides and allows self-assembly of the peptides.

The self-assembling peptide for use in the method of the present invention preferably comprises the sequence of the formula X1-X2-X1-X2-X1, wherein X1 is an amino acid with an acidic side chain, and X2 is an amino acid with a hydrophobic side chain selected from the group consisting of alanine, valine, isoleucine, leucine, methionine, phenylalanine, tyrosine, and tryptophan (SEQ ID NO: 3). In a more preferred embodiment, the self-assembling peptide for use in the method of the present invention comprises the sequence Glu-X2-Glu-X2-Glu, wherein X2 is an amino acid with a hydrophobic side chain selected from the group consisting of alanine, valine, isoleucine, leucine, methionine, phenylalanine, tyrosine, and tryptophan (SEQ ID NO: 4) or Asp-X2-Asp-X2-Asp, wherein X2 is an amino acid with a hydrophobic side chain selected from the group consisting of alanine, valine, isoleucine, leucine, methionine, phenylalanine, tyrosine, and tryptophan (SEQ ID NO:5). In another preferred embodiment, the self-assembling peptide for use in the method of the present invention comprises or consists of the sequence Gln-Gln-Arg-Phe-Glu-Trp-Glu-Phe-Glu-Gln-Gln, (P11-4, SEQ ID NO:1) or a sequence having at least 80% sequence identity thereto. It is further preferred that the peptide for use in the method of the present invention is modified P11-4 as shown in SEQ ID NO:2 or a sequence having at least 80% sequence identity thereto.

For the peptides referred to herein as P11-4, the switch from the monomeric to the assembled, multimeric form is controlled by the pH. If the pH is below pH 7.5, the peptide assembles. If the pH is higher, the state of the peptide is monomeric.

The peptide sequence having at least 80% or more sequence identity to SEQ ID NO:1 or 2 preferably comprises glutamic acid, or aspartic acid at positions which correspond to amino acids 5, 7 and 9 of SEQ ID NO:1 or 2. Specifically, the peptide sequence having at least 80% or more sequence identity to SEQ ID NO:1 preferably comprises glutamic acid at positions which correspond to amino acids 5, 7 and 9 of SEQ ID NO:1. Preferably, the remaining amino acid positions are amino acids with a hydrophobic side chain selected from the group consisting of alanine, valine, isoleucine, leucine, methionine, phenylalanine, tyrosine, and tryptophan. Preferably, the remaining amino acid positions are not amino acids that have basic side chains, i.e. amino acids that would be positively charged at a pH around neutral.

In one embodiment, the peptides of the invention comprise or consist of sequences that differ from those depicted in SEQ ID NOs:1 and 2 by the replacement of 1, 2 or 3 amino acids. Generally, each of the amino acid residues within the peptide sequence of SEQ ID NOs:1 and 2 may be substituted by another residue, as long as the resulting peptide is still capable of undergoing self-assembly at a pH value below 7.5. It is preferred that the substitutions are conservative substitutions, i.e. substitutions of one or more amino acid residues by an amino acid of a similar polarity, which acts as a functional equivalent. Preferably, the amino acid residue used as a substitute is selected from the same group of amino acids as the amino acid residue to be substituted. For example, a hydrophobic residue can be substituted with another hydrophobic residue, or a polar residue can be substituted with another polar residue having the same charge. Functionally homologous amino acids which may be used for a conservative substitution comprise, for example, non-polar amino acids such as glycine, valine, alanine, isoleucine, leucine, methionine, proline, phenylalanine, and tryptophan. Examples of uncharged polar amino acids comprise serine, threonine, glutamine, asparagine, tyrosine and cysteine. Examples of charged polar (basic) amino acids comprise histidine, arginine and lysine. Examples of charged polar (acidic) amino acids comprise aspartic acid and glutamic acid.

Figure 1:
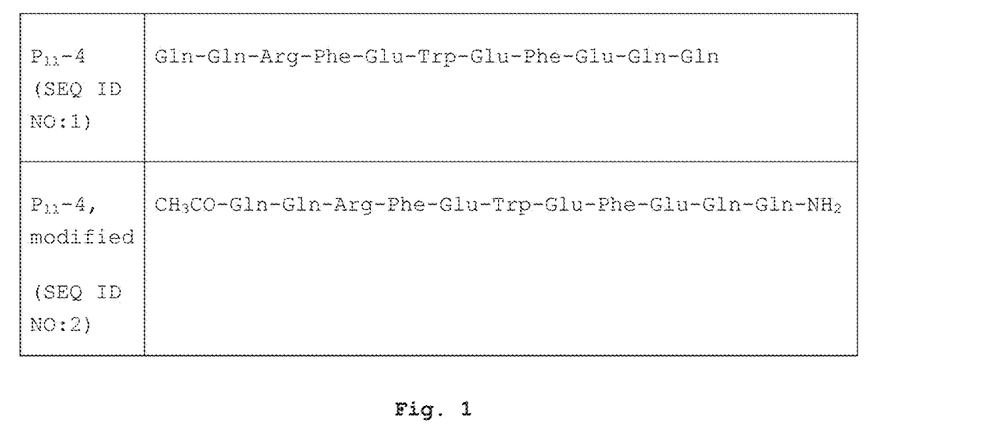
FIG. 1 depicts the sequences of the self-assembling peptide P11-4 (SEQ ID NO:1) and a sequence of P11-4 that has been N- and C-terminally modified (SEQ ID NO:2).

Further, the peptides of the invention may be structurally modified in one or more amino acid positions, e.g. by the introduction of one or more modified amino acids. According to the invention, these modified amino acids may be amino acids that have been changed by e.g. biotinylation, phosphorylation, glycosylation, acetylation, branching and/or cyclization. Further, the peptides of the invention may additionally or alternatively contain other modifications, such as terminal blocking groups, formyl-, gamma-carboxyglutamic acid hydroxyl-, methyl-, phosphoryl-, pyrrolidone carboxylic acid-, and/or sulphate-groups. In a preferred embodiment, the peptides of the present invention are acetylated at their N-terminus and/or amidated, e.g. with an $NH_2$-group, at their C-terminal end. A particularly preferred embodiment is a peptide P11-4 that is N-terminally acetylated and C-terminally amidated with a $NH_2$-group, as depicted in the following sequence: $CH_3CO$-QQR-FEWEFEQQ-$NH_2$ (SEQ ID NO:2) and in FIG. 1.

It is known to the skilled person that the peptide concentration may influence the assembly of peptides, i.e. a particularly high peptide concentration may trigger assembly ahead of time. Further, an exceptionally low peptide concentration may prevent assembly of the peptides of the invention, i.e. even under low pH conditions as present in tooth lesions and the oral cavity. Therefore, the peptide concentration in the solution of step a) will be between 0.1 to 100 mg/ml, 0.5 to 50 mg/ml, between 1 to 40 mg/ml, between 1 to 30 mg/ml, or between 1 to 20 mg/ml, or between 1 to 10 mg/ml. In a particularly preferred embodiment, the peptide concentration in the solution of step a) will be between 1 to 10 mg/ml. In a further preferred embodiment, the peptide concentration in the solution of step a) will be about 2 mg/ml.

The solution mentioned in step a) of the above method which contains the one or more self-assembling peptides has a pH which is 0.1 to 1.5, preferably 0.1 to 1.0, 0.1 to 0.5, 0.2 to 0.4, and more preferably about 0.3 units above the pH at which the peptide starts to undergo self-assembly which means that the pH of the peptide-containing solution is slightly higher than the pH at which assembly of a solution of monomers of said peptide is initiated. In a preferred embodiment, the solution mentioned in step a) has a pH which is 0.3 pH units above the pH at which the peptide starts to undergo self-assembly. In a particularly preferred embodiment, the solution comprises the peptide P11-4 (SEQ ID NO:1) or modified P11-4 as shown in SEQ ID NO:2 and the solution has about pH 7.8 or higher in step a) of the above method. The solution is preferably an aqueous solution. However, the solution may also contain amounts of other solvents, such as an organic or inorganic solvent, i.e. an alcohol, ether, ketone.

Keeping the solution in step a) at a pH above the pH at which the peptide starts to undergo self-assembly as described above is optimal for the self-assembling peptides to remain in their monomeric form once they have been detached from one another by an initial raise in the pH. This pH is slightly above the pH at which the self-assembly of the peptide starts. The solution of step a) preferably contains one or more buffers for maintaining the pH of the solution of step a) in the desired range. In a preferred embodiment, the solution of step a) is buffered to a pH which is 0.1 to 0.5 pH units higher than the pH at which the peptide starts to undergo self-assembly. The buffer which provides the pH which is 0.1 to 0.5 pH units above the pH at which the peptide starts to undergo self-assembly is an essentially non-volatile buffer, so that the buffer will remain in the composition during and after lyophilisation. Preferably, the solution contains a buffer to provide a pH which is 0.1 to 0.5 pH units above pH 7.5.

Suitable buffers include TAPS ({[tris(hydroxymethyl)methyl]amino}propanesulfonic acid), Bicine (N,N-bis(2-hydroxyethyl)glycine), Tris(Tris(hydroxymethyl)-aminomethan), Tricine (N-tris(hydroxymethyl)methylglycine), TAPSO (3-[N-Tris(hydroxyl-methyl)methylamino]-2-hydroxypropanesulfonic acid), HEPES (4-2-hydroxyethyl-1-piperazineethanesulfonic acid), TES (2-{[tris(hydroxymethyl)methyl]amino}ethanesulfonic acid), MOPS (3-(N-morpholino) propanesulfonic acid), PIPES (piperazine-N,N'-bis(2-ethanesulfonic acid)), Cacodylate (dimethylarsinic acid), SSC (saline sodium citrate), MES (2-(N-morpholino) ethane-sulfonic acid), and other buffers that maintain an essentially neutral pH range. Acid buffers, such as citric acid, phosphoric acid, and others may also be used in conjunction with any of the above buffers and/or an alkaline buffer, such as sodium hydroxide, potassium hydroxide, ammonium hydroxide, sodium phosphate di- and tri-basic, potassium phosphate di- and tri-basic, sodium tripolyphosphate, Tris, triethanolamine, poly-ethylenimine, to obtain the desired pH which is 0.1 to 0.5 pH units above the pH at which the peptide starts to undergo self-assembly and to provide buffering capacity. In a preferred embodiment, the buffer to provide a specific pH which is 0.1 to 0.5 pH units above the pH at which the peptide starts to undergo self-assembly, such as pH 7.5, is Tris.

The buffer used for preparing the solution of step a) will have a concentration that is sufficient to provide a pH which is 0.1 to 0.5 pH units above the pH at which the peptide starts to undergo self-assembly. At the same time, the buffer concentration will be as low as possible so that a low ionic strength after lyophilisation is provided. In a preferred embodiment, the concentration of the buffer in the solution of step a) is less than 200 mM, less than 150 mM, less than 100 mM, less than 50 mM, less than 40 mM, less than 30 mM, less than 20 mM, or less than 10 mM. In a further preferred embodiment, the buffer is TRIS in a concentration of less than 200 mM, less than 150 mM, less than 100 mM, less than 50 mM, less than 40 mM, less than 30 mM, less than 20 mM, or less than 10 mM. In a preferred embodiment, the buffer is TRIS in a concentration of about 4 mM.

The solution of step a) may further comprise additional components, such as e.g. a salt, such as e.g. NaCl. As is known to the skilled person, the assembly state of peptides is influenced also by the ionic strength in the solution. The ionic strength of a solution is a function of the concentration of all ions present in that solution. Thus, even at a pH above the pH at which the peptide starts to undergo self-assembly, i.e. when the peptide is substantially monomeric in solution, a particularly high ionic strength might be able to trigger the assembly of the peptide. However, assembly of the peptides of the present invention is advantageously not triggered when the ionic strength is in the physiological range, i.e. corresponding to or below the ionic strength corresponding to 150 mM NaCl. The skilled person will know how to determine and measure the ionic strength of a solution. The ionic strength I is generally calculated according to the formula $I=1/2\Sigma\ z_i^2 b_i$, wherein z is the valence factor and $b_i$ is the molality [mol/kg{$H_2O$}] of the $i^{th}$ ion concentration. The summation, $\Sigma$, is taken over all ions in the solution. For example, the ionic strength of a 150 mM NaCl solution is approximately 0.15. This is also approximately the ionic strength of blood. The ionic strength of saliva present in the oral cavity is generally much lower, such as e.g. approximately 0.04. Thus, in a preferred embodiment, the ionic strength of the solution of step a) is less than 0.15, less than 0.1, less than 0.05, or less than 0.025. In a preferred embodiment, the ionic strength of the solution of step a) is less than 0.15. In a further preferred embodiment, the solution is less than 0.1.

The skilled person is aware of numerous methods to determine the ionic strength of a solution. For example, the ionic strength may be estimated from a measurement of the electric conductance (S=1/$\Omega$=A/V) of a solution via the Russell's factor as follows: $I=1.6\times10^{-5}\times$Specific Conductance [$\mu$S/cm]. A 150 mM NaCl solution has a conductance of approximately 80-100 mS/cm. Thus, according to the above and the described estimation of the electric conductance, the solution of step a) will have an electric conductance of below 100 mS/cm, preferably below 80 mS/cm.

Further, the skilled person is aware of numerous methods to determine the pH at which a peptide of the present invention will start self-assembly at a given ionic strength. Suitable methods are denoted e.g. in a publication by Aggeli et al. (2003, J Am Chem Soc, 125, 9619-9628).

In step b) of the above method, a basic compound that increases the pH of the solution to 8.0 or higher is added to the solution. Preferably, said pH in step b) is increased to pH 8.0 or higher, preferably to 8.0-9.5, more preferably to pH 8.5. The basic compound is partially or completely volatile, so that it is removed during lyophilisation by evaporating together with the water. In a preferred embodiment, more than 70%, more than 80%, more than 90%, more than 95%, more than 96%, more than 97%, more than 98%, and even more preferably more than 99% of the volatile compound are removed in step c). If traces of the compound remain in the lyophilisate, these amounts will not suffice to increase the pH by more than 0.3 pH units after reconstitution of the lyophilisate in comparison to the same solution without any of the compound. Suitable basic compounds for increasing the pH in step b) of the method of the present invention include, but are not limited to, e.g. ammonia ($NH_3$), 2-aminoethanol (monoethanolamine), 4-methylmorpholine and pyridine. The use of ammonia in step b) of the method of the invention is particularly preferred.

The skilled person will be able to determine which concentration of the basic compound is required to increase the pH of the solution to 8.0 or higher. The pH can be determined upon addition of the basic compound by routine methods. For example, in a simple approach, the pH in solution may be determined by using a pH indicator, such as Bromthymol blue, a pH meter, or pH strips. The compound that increases the pH will be added to the solution until a pH of 8.0 or higher is reached. Preferably, the compound that increases the pH will be added until a pH of at least 8.0, at least 8.2, at least 8.4, at least 8.6, at least 8.8, at least 9.0 is reached.

In step b) of the method of the invention, the pH will be increased until essentially all of the self-assembling peptides are in a monomeric form. The skilled person will be able to determine whether essentially all of the self-assembling peptides are in a monomeric form by means of routine experimentation. For example, the assembly state of the peptides in solution can be determined by nuclear magnetic resonance (NMR), such as $^1$H-NMR, by circular dichroism analysis, by dynamic light scattering (DLS) analysis, diffusing-wave spectroscopy, native electrophoretic methods, Fourier transform infrared spectroscopy (FTIR), viscosity measurements (rheology), and the like.

Figure 3:
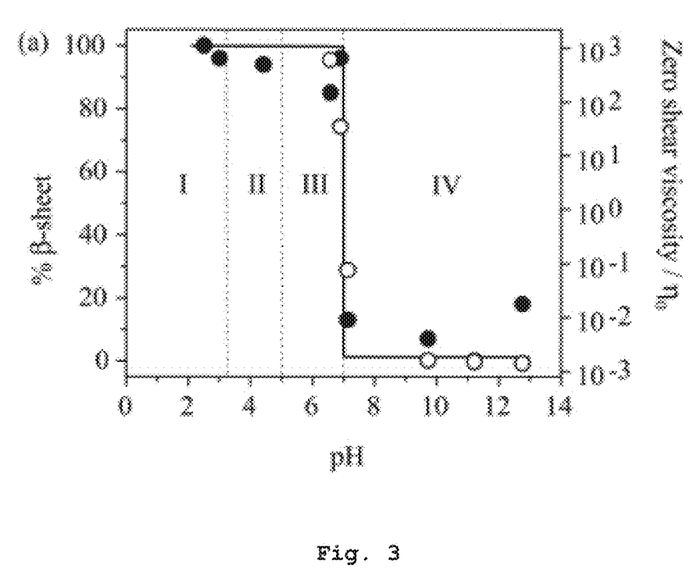

Further, the assembly state may also be estimated on the basis of the viscosity of the resulting solution because an assembly to a considerable extend will change the viscosity of the peptide solution. For example, in an aqueous solution the peptide P11-4 (SEQ ID NO:1) is present as an isotropic fluid above pH 7.5, as a nematic fluid between about pH 7.5 and about pH 5, a flocculate between about pH 5 and about pH 3 and a nematic gel below pH 3 (Aggeli et al., 2003, J Am Chem Soc, 125:9619-9628; FIG. 3), corresponding to the self-assembly of the peptide with decreasing pH. The viscosity of the solution may be estimated by visual inspection of the flowing properties of the solution. For example, while an isotropic fluid may be ejected efficiently through a needle, this will not be the case for more viscous phases. When the peptides of the present invention are essentially monomeric in solution, i.e. the solution is present as an isotropic fluid, then the solution has a relatively low viscosity which facilitates easy ejection of the solution through a needle. For example, when the peptides of the present invention are essentially monomeric in solution, then the solution may be readily ejected through a needle with a diameter of e.g. 1.6 mm or 1.1 mm.

To prevent degradation and/or precipitation of the peptides in solution the pH will normally not be increased to a value higher than 10.5. It is commonly known that the chemical properties of a peptide depend on the amino acid sequence. For example, reversible oxidation of cysteine and methionine residues may be accelerated at higher pH, where the thiol is more easily deprotonated and readily forms intra-chain or interchain disulfide bonds. The skilled person will be aware of amino acid side chains that are detrimentally affected by a basic pH and be able to determine the maximal pH that keeps the integrity of the self-assembling peptide intact by routine experimentation. For example, this maximal pH may be predicted on the basis of the known properties of each amino acid present in the peptide. Alternatively, biochemical methods, such as electrophoretic methods, may be employed to determine the integrity of the peptide. Preferably, the pH in step b) will be between 8.0 and 10.5, more preferably between 8.0 and 10.0, and most preferably between 8.0 and 9.5 after addition of the basic compound. Further, the pH in step b) may be between 8.5 and 10.5 or between 8.5 and 10.0.

Further, as described above for the solution of step a), the ionic strength of the solution in step b) will not be increased to more than 0.15 by the addition of the above defined basic compound to prevent assembly of the peptides of the invention. Thus, the ionic strength of the solution of step b) will be less than 0.15, less than 1.0, less than 0.05, or less than 0.025. In a preferred embodiment, the ionic strength of the solution of step b) is less than 0.15. In a further preferred embodiment, the solution is less than 0.1. All comments made above with respect to the ionic strength of the solution of step a) do also apply to the solution of step b).

In one embodiment of the invention, a filtration step b1) is added between step b) and step c) of the above method to sterilize the peptide solution. Any filtration technique known in the art can be used in the method of the invention. As the filtration of peptide solutions is a routine measure, the skilled person will be able to determine the necessary filter types, pore sizes and an efficient filtration routine without inventive activity.

In a further embodiment, the peptide solution of step b) or b1) is filled into a container in a filling step b2). Filling step b2) is preferably carried out between step b) and step c), or between step b1) and step c). It is preferred that a defined volume of the peptide solution is filled into a container. The defined volume is e.g. between about 5 µl and 1 ml, between about 5 µl and 500 µl, or between about 10 µl and 250 µl. For example the defined volume is preferably below 1 ml, below 500 µl, below 250 µl or below 50 µl. However, the defined volume may of course also be larger than 1 ml. Filling may be carried out with a pipette, tubing or a syringe or the like. The peptide solution may be filled into the container manually, e.g. by pipetting of the solution, or automatically, e.g. in a high-throughput facility.

The container may be of any nature that is suitable to contain a liquid peptide solution. For example, the container may be a vial. Preferably, the vial or container is made of glass or hard plastic. The vial or container material is preferably chemically inert and will not react considerably with the peptide solution. It is further preferred that the peptide solution does not or essentially not stick to the walls of the container. The material can therefore have electrostatic properties which would prevent adhesion of the peptides to the material.

In a preferred embodiment, steps b1) and b2) are carried out as a combined step, i.e. the defined volume of the peptide solution is filtrated into the container.

The container or vial will preferably be closed after lyophilization in step d). For example, the container or vial can be capped or sealed. Suitable caps and seals are known in the art.

In step c) of the above method, the solution will be lyophilized. Any lyophilisation process known in the art can be used in the method of the invention. Lyophilization generally includes three main stages: freezing, primary drying and secondary drying. Freezing converts water to ice or some amorphous composition components to the crystalline form. Primary drying is the process step when ice is removed from the frozen product by direct sublimation at low pressure and temperature. Secondary drying is the process step when bounded water is removed from the product matrix utilizing the diffusion of residual water to the evaporation surface. Any kind of freeze-dryer may be used for lyophilisation, e.g. a manifold freeze-dryer, a rotary freeze-dryer, a multi-shelve freeze-dryer or a tray style freeze-dryer.

The solution which comprises the self-assembling peptides and is subjected to lyophilization may also contain excipients such as stabilizers, bulking agents, and/or surfactants that turn out to be useful for preventing the peptides from degradation during freeze-drying and/or storage or support rehydration of the dried peptide. Therefore, appropriate excipients may be added prior to step c) to prevent proteins from dehydration stress during lyophilization, to enhance protein stability during freeze-drying, to improve cake (i.e. lyophilisate) stability and/or to improve the stability of lyophilized peptides during storage. Preferably, the excipients are added between step a) and step b). In particular, the excipients have the effect that the peptides essentially retain their physical and chemical stability and their monomeric state during lyophilization and/or storage.

Typically, a suitable excipient is a non-charged and/or non-reducing sugar such as sucrose, raffinose, trehalose, mannitol, sorbitol, or derivatives thereof, such as trehalose dihydrate, or an amino acid, such as glycine, arginine and methionine. Further suitable stabilizing agents include citric acid, sodium bicarbonate, EDTA, benzylalcohol, sodium chloride or lactose. In a preferred embodiment, the added stabilizing or bulking agent is a non-reducing sugar selected from the group comprising mannitol, sorbitol, sucrose, trehalose, and glycine, or derivatives thereof, such as trehalose dihydrate. In a particularly preferred embodiment, trehalose dihydrate is added in the method of the invention prior to step c).

The amount of stabilizing and/or bulking agent in the pre-lyophilized solution will depend on the specific peptides and the components used in the composition to be lyophilised. Typical amounts to be used, for example for a non-reducing sugar include 0.1-5%, preferably 1-4%, more preferably 2-3% of any of the solutions of steps a), b) or d). Suitable amounts to be used, for example for a non-reducing sugar, such as Trehalose dihydrate, include about 1 to 30 mg/ml, about 5 to 20 mg/ml, such as about 10 mg/ml.

The composition obtained from step c) is a lyophilisate that is suitable for shipping and storing, as it is highly stable in that the peptides are protected from degradation or undesired self-assembly. Thus, in one embodiment of the method of the invention, the lyophilisate is dissolved in an aqueous solution to obtain a solution with a pH that is 0.1 to 0.5 pH units above the pH at which the peptide starts to undergo self-assembly comprising the peptide in its monomeric state. For example, when using the lyophilisate for treating a caries lesion, e.g. by a dentist, an aqueous solution, such as water, is added to the lyophilisates to obtain a final solution having a pH that is 0.1 to 0.5 pH units above the pH at which the peptide starts to undergo self-assembly comprising the peptide in its monomeric state. The lyophilisate is preferably dissolved in plain water, more preferably in deionized water. However, the lyophilisate may be dissolved in any kind of aqueous solution as long as the resulting solution has a pH that is 0.1 to 0.5 pH units above the pH at which the peptide starts to undergo self-assembly comprising the peptide in its monomeric state. In a preferred embodiment, the aqueous solution, such as water, will have an ionic strength corresponding to an electric conductance of less than 5 mS/cm at 25° C. In case a non-volatile buffer was present in the solution of step a) it is still present in the lyophilisate.

The lyophilisate will preferably be dissolved in a volume sufficient to result in a peptide concentration of between 0.1 to 100 mg/ml, between 0.5 to 50 mg/ml, between 1 to 40 mg/ml, between 1 to 30 mg/ml, between 1 to 20 mg/ml, or between 1 to 10 mg/ml. In a particularly preferred embodiment, the lyophilisate will preferably be dissolved in a volume sufficient to result in a peptide concentration of between 1 to 10 mg/ml. In a further preferred embodiment, the lyophilisate will preferably be dissolved in a volume sufficient to result in a peptide concentration of about 2 mg/ml.

Further, as described above for the solution of step a), the ionic strength of the solution of step d) will be less than 0.15, less than 0.1, less than 0.05, or less than 0.025. In a preferred embodiment, the ionic strength of the solution of step d) is less than 0.15. In a further preferred embodiment, the solution is less than 0.1. All comments made above with respect to the ionic strength of the solution of step a) do also apply to the solution of step d).

It is preferred that the lyophilisate is dissolved immediately before application to the tooth in order to minimize the time in which the peptides are in solution. In particular, it is preferred that the lyophilisate is dissolved within 1 hour before use, preferably about 45 minutes before use, about 45 minutes before use, about 45 minutes before use, about 30 minutes before use, about 25 minutes before use, about 20 minutes before use, about 15 minutes before use, about 10 minutes before use, and even more preferably about 5 minutes or less before use.

In a further aspect, the present invention provides a composition, e.g. a composition for treating a caries lesion and/or a composition for remineralising a tooth surface and/or a caries lesion. The composition is preferably a composition in lyophilized form for reconstitution which comprises one of the above described peptides that undergoes self-assembly at a pH value below 7.5, wherein by reconstitution of the lyophilisate, a solution with a pH that is 0.1 to 0.5 pH units above the pH at which the peptide starts to undergo self-assembly is obtained in which the peptide is predominantly present in a monomeric form. As described above, the peptide preferably comprises the sequence X1-X2-X1-X2-X1, wherein X1 is an amino acid with an acidic side chain, and X2 is an amino acid with a hydrophobic side chain selected from the group consisting of alanine, valine, isoleucine, leucine, methionine, phenylalanine, tyrosine, and tryptophan. It is further preferred that the peptide comprises the sequence Glu-X2-Glu-X2-Glu or Asp-X2-Asp-X2-Asp, wherein X2 is an amino acid with a hydrophobic side chain selected from the group consisting of alanine, valine, isoleucine, leucine, methionine, phenylalanine, tyrosine, and tryptophan. For example, the compositions may comprise a peptide comprising the sequence depicted in SEQ ID NO:1 or SEQ ID NO:2 or a sequence having at least 80% sequence identity thereto.

In a preferred embodiment, at least 70%, preferably at least 80%, more preferably at least 90%, of the peptides are present in monomeric form.

The composition of the present invention is preferably obtained by the above described method. In one embodiment, the present invention provides a composition comprising the lyophilisate obtained in step c) of the method of the invention or the reconstituted solution obtained in step d) of said method.

The composition can be mixed with additional compounds that assist in the administration of the monomeric peptides to the site of treatment, i.e. the tooth lesion or cavity. For example, the reconstituted solution obtained in step d) can be mixed with a vehicle such as a hydrogel. In the context of the present invention, a hydrogel refers to a network of covalently or non-covalently interconnected polymers that are insoluble in water but absorb water and undergo swelling which leads to a considerable volume increase. Preferably, the volume increase upon swelling is 10%, 15%, 20%, 25%, 30%, 35%, 40%, 45%, 50% or more. Preferred hydrogels comprise or consist of hyaluronic acid or polyurethane. Hydrogels for use in pharmaceutical applications are commonly known and can be purchased from different manufacturers.

The invention also provides a method for treating a caries lesion, preferably a subsurface caries lesion, wherein a composition of the present invention is administered to a patient in need thereof. In a still further aspect, the invention provides a method for remineralising a tooth surface and/or a caries lesion, preferably a subsurface caries lesion, wherein a composition of the present invention is administered to a patient in need thereof.

Thus, the above described compositions may be used in a method of treating a caries lesion, preferably a subsurface caries lesion. In a preferred embodiment, the above compositions are used in a method of remineralising a tooth surface and/or a caries lesion, preferably a subsurface caries lesion.

The compositions of the invention may be applied to the tooth which is in need of a treatment directly by the medical practitioner, or by means that provide some isolation of the pharmaceutical compositions from the acidic environment in the oral lesion. For example, the compositions may be applied with the help of liquid drug transfer devices, such as those described in WO 2011/104712 A1, WO 2011/104711 A1, WO 2011/058545, WO 2005/105014 A2. The liquid drug transfer devices may e.g. comprise sealing arrangements which separate the compositions from the acidic environment in the oral lesion.

BRIEF DESCRIPTION OF THE FIGURES

FIG. 3 shows the phase behaviour of P11-4 (c=6.3 mM) as a function of pH (DCl/NaOD): I=nematic gel, II=flocculate, III=nematic fluid, IV=isotropic fluid. ○=zero shear viscosity, and ●=% β-sheet determined using FTIR spectroscopy: the continuous line denotes the proportion of peptide in fibrils. The broken vertical lines separating regions I, II, and III denote approximate boundaries between different macroscopic fibrillar states, while that separating regions III and IV denotes a first order nematic-to-isotropic transition. (Figure replicated with permission from Aggeli et al. (2003, J am ChemSoc, 125, 9619-9628).)

The method of the invention is exemplified in more detail in the following examples.

EXAMPLES

Example 1

Preparation of Peptide Solutions

Modified P11-4 peptide with the sequence depicted in SEQ ID NO:2 was thawed 24 hours before use at 5+/−3° C. 4 mM Tris are added to water of the WFI (water for injection) grade under stirring for at least 10 minutes at room temperature. Trehalose-Dihydrate is added under continued stirring to a final concentration of 10 mg/g. Subsequently, the peptide P11-4 is added to a final concentration of 2 mg/ml and dissolved under stirring to clarity. This peptide solution initially has a pH of about 8.2.

The pH of the peptide solution is adjusted to 8.5 +/−0.4 with 1% NH$_4$OH solution.

The peptide solution is subsequently filtered sterile through Sartopore filters. The sterile solution is filled into vials which are then submitted to lyophilisation in a multi shelve freeze-drier. After freezing for 1 to 3 h at −45° C., the vials are submitted to a main drying step at 30° C. for 10 to 13 h and a after drying step at 30° C. for 7 to 10 h. Airing is supplied with nitrogen at 200 to 800 mbar. The vials are closed at 30° C. and 200 mbar and capped for transport.

The vials are subsequently inspected visually for integrity of the cake (i.e. the lyophilisate).

Figure 2:
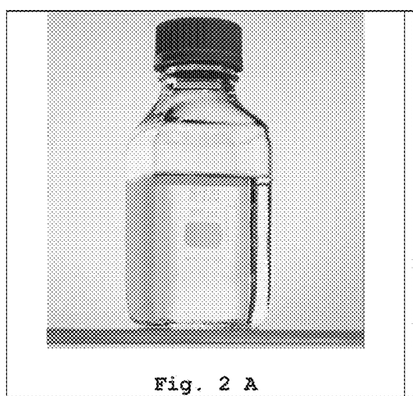
FIGS. 2A to 2D show example compositions in bulk solution prior to lyopilization (FIG. 2A), after filling prior to lyophilization (FIG. 2B) and after lyophilisation (FIGS. 2C and 2D). The compositions in FIG. 2B have been stained solely for the purpose of visualization.

Results: The peptide solution was in the form of a nematic viscoelastic fluid after dissolution. After adjusting the pH to 8.5, the peptide solution appeared clear and non-viscous as an isotropic fluid (FIG. 2 A). After filling of the solution into vials, the solution still appeared clear and non-viscous (FIG. 2B: example aliquots which were stained blue solely for visualization of the solution). Lyophilization lead to an intact "cake", i.e. lyophilisate, (FIG. 2C) that showed good storage stability.

Example 2

Preparation of Peptide Solutions with Different Concentrations

As described above, peptide solutions with different buffer (TRIS), peptide (P11-4) and bulking agent (Trehalose-Dihydrate) concentrations were prepared. The pH was adjusted as described above.

| Example | Peptide conc [mg * ml−1] | Bulking Agent [mg * ml−1] | Buffer [mM] |
|---|---|---|---|
| 1 | 1 | 50 | 4 |
| 2 | 2 | 25 | 5 |
| 3 | 4 | 10 | 6 |

Results: After filling of the solution into vials, all three solutions appeared clear and non-viscous. Lyophilization lead to an intact "cake", i.e. lyophilisate, that showed good storage stability.

Example 3

Viscosity of P11-4 Peptide Solution

To estimate the assembly state in a peptide solution, passage of the P11-4 peptide solution through different filling needles was tested.

Composition of P11-4 Bulk Solution

A P11-4 bulk solution was compounded as follows:

TABLE 1

Table 1 shows the composition of the solution.

| Substances | Weight [g] | Concentration in final solution [mg/g] |
|---|---|---|
| P11-4 | 0.500 | 2 |
| Trehalose dihydrate | 2.5 | 10 |
| TRIS | 0.121 | 0.484 |
| add. to with dist. Water | 250 | / |

P11-4, trehalose dihydrate (Hayashibara Co. Ltd., Lot Nr. 9D081) and TRIS (Carl Roth, A411.1) were dissolved in approximately 200 g purified water. The pH was adjusted to 8.5 using about 0.5 mL 1% NH3-solution. Final weight of the bulk solution was adjusted with purified water to 250 g.

The solution was then filtered using an Acrodisc® 25 mm syringe filter (0.22 μm Fluorodyne® II membrane) connected to a peristaltic pump (520Di, Watson-Marlow Pumps Group, Falmouth, United Kingdom) delivering the bulk solution at a pump speed of 10 rpm.

Density of the Peptide Solution

P11-4 bulk solution was compounded and the density of the solution was determined using a DMA300 portable density meter (Anton Paar Germany GmbH, Ostfildern, Germany). Bulk solution was filled into the density meter using a syringe. Temperature compensation to 25° C. was automatically performed by the density meter.

Density measurements of the peptide solution were performed. The solution reached a density of 1.001 mg/mL at 25° C., n=2.

Viscosity of the Peptide Solution

The EDM 3295 dosing machine (Bausch+Strobel Maschinenfabrik GmbH+Co. KG, Ilshofen, Germany) was adjusted to a filling weight of 250 mg. Test inlay vials were weighted empty, filled with bulk solution and weighted again after filling.

Table 2 gives the results for the test filling using filling needle 443009L (Ø1.6 mm, length 96 mm; material code: AI-SI316L).

TABLE 2

| Statistical evaluation test filling using filling needle 443009L (Ø 1.6 mm) | |
|---|---|
| Average [mg] | 248.4 |
| SD [mg] | 0.3 |
| Rel. SD [%] | 0.1 |
| 2 × SD [mg] | 0.7 |
| 2 × rel. SD [%] | 0.3 |
| Minima [mg] | 248.0 |
| Maxima [mg] | 249.3 |
| n | 20 |

Table 3 gives the results of the test filling using filling needle 443008L (Ø1.1 mm, length 96 mm; material code: AI-SI316L)

TABLE 3

Statistical evaluation test filling using filling needle 443008L (Ø 1.1 mm)

| | |
|---|---|
| Average [mg] | 248.7 |
| SD [mg] | 0.3 |
| Rel. SD [%] | 0.1 |
| 2 × SD [mg] | 0.7 |
| 2 × rel. SD [%] | 0.3 |
| Minima [mg] | 248.2 |
| Maxima [mg] | 249.4 |
| n | 20 |

Both filling needles showed a comparable filling accuracy of less than 1.0 mg, i.e. a minimal loss of substance, at a filling weight of 250 mg. Consequently, the peptide solution was able to pass efficiently through both needles. Essentially no clogging of the needle occurred. The viscosity of the solution was low enough to allow needle passage. This indicates that the peptide solution is present as an isotropic fluid (compare Aggeli et al., 2003, J Am Chem Soc, 125: 9619-9628 for the phase behaviour of peptide P11-4 as a function of the pH).

The invention claimed is:

1. A composition in lyophilized undissolved form comprising
    a peptide that undergoes self-assembly at a pH value below 7.5, wherein the peptide is predominantly in a monomeric form;
    a non-reducing sugar; and
    a non-volatile buffer;
    wherein upon reconstitution of the composition in water, a solution with an ionic strength of less than 0.15 and a pH that is 0.1 to 0.5 pH units above the pH at which the peptide starts to undergo self-assembly is obtained in which the peptide is predominantly present in a monomeric form.

2. The composition of claim 1, wherein said peptide comprises the sequence of SEQ ID NO:3.

3. The composition of claim 1, wherein said peptide comprises the sequence of SEQ ID NO: 4 or SEQ ID NO: 5.

4. The composition of claim 1, wherein said peptide comprises the sequence depicted in SEQ ID NO:1 or SEQ ID NO:2 or a sequence having at least 80% sequence identity thereto.

5. The composition of claim 1, wherein at least 70% of the peptide are present in monomeric form.

6. The composition of claim 1, wherein at least 80% of the peptide are present in monomeric form.

7. The composition of claim 1, wherein at least 90% of the peptide are present in monomeric form.

* * * * *

UNITED STATES PATENT AND TRADEMARK OFFICE
CERTIFICATE OF CORRECTION

| | | |
|---|---|---|
| PATENT NO. | : 10,464,968 B2 | Page 1 of 1 |
| APPLICATION NO. | : 16/025344 | |
| DATED | : November 5, 2019 | |
| INVENTOR(S) | : Michael Hug and Dominikus Amadeus Lysek | |

It is certified that error appears in the above-identified patent and that said Letters Patent is hereby corrected as shown below:

In the Claims

Column 19, Claim 1, Line 1, delete "lyophilized."

Signed and Sealed this
Twenty-fourth Day of March, 2020

Andrei Iancu
*Director of the United States Patent and Trademark Office*